(12) United States Patent
Billodeaux et al.

(10) Patent No.: US 9,382,179 B2
(45) Date of Patent: *Jul. 5, 2016

(54) NICKEL MODIFIED CATALYST FOR THE PRODUCTION OF HYDROXY ETHER HYDROCARBONS BY VAPOR PHASE HYDROGENOLYSIS OF CYCLIC ACETALS AND KETALS

(71) Applicant: Eastman Chemical Company, Kingsport, TN (US)

(72) Inventors: Damon Ray Billodeaux, Raleigh, NC (US); Thomas James Devon, Longview, TX (US); Brent Alan Tennant, Kingsport, TN (US); Charles Edwan Sumner, Jr., Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,956

(22) Filed: Jun. 18, 2014

(65) Prior Publication Data

US 2014/0303404 A1    Oct. 9, 2014

Related U.S. Application Data

(63) Continuation of application No. 13/168,361, filed on Jun. 24, 2011, now Pat. No. 8,785,697.

(51) Int. Cl.
*C07C 41/28* (2006.01)

(52) U.S. Cl.
CPC .................................. *C07C 41/28* (2013.01)

(58) Field of Classification Search
CPC ........................................................ C07C 41/28
See application file for complete search history.

(56) References Cited

U.S. PATENT DOCUMENTS

| | | | |
|---|---|---|---|
| 2,425,042 A | 8/1947 | McNamee et al. |
| 2,429,878 A | 10/1947 | Gresham et al. |
| 2,486,024 A | 10/1949 | Hearne et al. |
| 3,275,680 A | 9/1966 | Holzrichter et al. |
| 4,024,159 A | 5/1977 | Peterson |
| 4,038,175 A | 7/1977 | Bhasin |
| 4,062,898 A | 12/1977 | Dubeck et al. |
| 4,071,568 A | 1/1978 | Onoda et al. |
| 4,088,700 A | 5/1978 | Watts |
| 4,169,959 A | 10/1979 | Arpe |
| 4,308,403 A | 12/1981 | Knifton |
| 4,317,943 A | 3/1982 | Knifton |
| 4,356,327 A | 10/1982 | Knifton |
| 4,357,477 A | 11/1982 | Knifton |
| 4,375,394 A | 3/1983 | Devon |
| 4,390,734 A | 6/1983 | Knifton |
| 4,430,253 A | 2/1984 | Dubeck |
| 4,435,595 A | 3/1984 | Agreda et al. |
| 4,478,017 A | 10/1984 | Brown et al. |
| 4,479,017 A | 10/1984 | Ayusawa et al. |
| 4,482,753 A | 11/1984 | Huang et al. |
| 4,484,009 A | 11/1984 | Ghenassia et al. |
| 4,537,980 A | 8/1985 | Greenshields |
| 4,568,780 A | 2/1986 | Knifton |
| 4,617,287 A | 10/1986 | Lyons |
| 4,618,729 A | 10/1986 | Duggan et al. |
| 4,663,489 A | 5/1987 | Duggan et al. |
| 4,692,426 A | 9/1987 | Duggan et al. |
| 4,847,425 A | 7/1989 | Degner et al. |
| 4,895,818 A | 1/1990 | Duggan et al. |
| 4,895,987 A | 1/1990 | Duggan et al. |
| 4,939,294 A | 7/1990 | Agreda et al. |
| 5,319,148 A | 6/1994 | Karcher et al. |
| 5,362,918 A | 11/1994 | Aizawa et al. |
| 5,399,631 A | 3/1995 | Egawa et al. |
| 5,446,208 A | 8/1995 | Koshino et al. |
| 5,446,210 A | 8/1995 | Hees et al. |
| 5,523,491 A | 6/1996 | Egawa et al. |
| 5,589,597 A | 12/1996 | Egawa et al. |
| 5,616,736 A | 4/1997 | Thigpen |
| 5,720,895 A | 2/1998 | Nakagawa et al. |
| 5,763,691 A | 6/1998 | Kawabe |
| 5,780,687 A | 7/1998 | Holderich et al. |
| 5,821,391 A | 10/1998 | Holderich et al. |
| 5,866,735 A | 2/1999 | Cheung |
| 5,886,198 A | 3/1999 | Ogawa et al. |
| 5,917,059 A | 6/1999 | Bruchmann et al. |
| 5,935,896 A | 8/1999 | Dupuis et al. |
| 6,013,844 A | 1/2000 | Heineke et al. |
| 6,015,875 A | 1/2000 | Smith et al. |
| 6,028,215 A | 2/2000 | Bessling et al. |

(Continued)

FOREIGN PATENT DOCUMENTS

CA    1 254 190    5/1989
DE    419223 C    9/1925

(Continued)

OTHER PUBLICATIONS

English translation of FR 2 906 246 A1, pp. 1-13.
USPTO Notice of Allowance dated Dec. 19, 2014 for co-pending U.S. Appl. No. 13/168,374.
USPTO Notice of Allowance dated Feb. 25, 2015 for co-pending U.S. Appl. No. 13/168,274.
Knifton "Syngas reactions: Part VIII: The preparation of glycol monoalkyl ethers," Journal of Molecular Catalysis 1985, 30, pp. 281-297.
Jakab et al. "Synthesis, regioselective hydrogenolysis, partial hydrogenation, and conformational study of dioxane and dkoxane-type (9-anthracenyl)methylene acetals of sugars," Carbohydrate Research 2009, 344, pp. 2444-2453.
Broekhuis et al. "Recovery of Propylene Glycol from Dilute Aqueous Solutions via Reversible Reaction with Aldehydes" Ind. Eng. Chem. Res. 1994, 33, pp. 3230-3237.
Dhale et al. "Propylene Glycol and Ethylene Glycol Recovery from Aqueous Solution via Reactive Distillation" Chemical Engineering Science, 2004, 59, pp. 2881-2890.

(Continued)

*Primary Examiner* — Rosalynd Keys
(74) *Attorney, Agent, or Firm* — Phan Law Group PLLC

(57) ABSTRACT

Catalyst compositions of alumina supports containing palladium and nickel are selective in a vapor phase hydrogenolyzis reaction to convert cyclic acetal compounds and/or cyclic ketal compounds in the presence of hydrogen to their corresponding hydroxy ether hydrocarbon reaction products.

15 Claims, No Drawings

(56) References Cited

U.S. PATENT DOCUMENTS

| | | | |
|---|---|---|---|
| 6,080,897 | A | 6/2000 | Kawabe |
| 6,087,539 | A | 7/2000 | Yamasaki et al. |
| 6,124,479 | A | 9/2000 | Hinoue et al. |
| 6,136,576 | A | 10/2000 | Diaz-Torres |
| 6,143,908 | A | 11/2000 | Hinoue et al. |
| 6,166,240 | A | 12/2000 | Jiang et al. |
| 6,207,850 | B1 | 3/2001 | Jiang et al. |
| 6,232,512 | B1 | 5/2001 | Haas et al. |
| 6,265,623 | B1 | 7/2001 | Morawietz et al. |
| 6,291,725 | B1 | 9/2001 | Chopade |
| 6,380,419 | B2 | 4/2002 | Kawabe |
| 6,458,992 | B1 | 10/2002 | Lederer et al. |
| 6,518,464 | B2 | 2/2003 | Therre et al. |
| 6,548,681 | B1 | 4/2003 | Chopade et al. |
| 6,657,089 | B1 | 12/2003 | Nagasawa et al. |
| 6,670,489 | B2 | 12/2003 | Koyama et al. |
| 6,713,640 | B2 | 3/2004 | Miller et al. |
| 6,969,779 | B2 | 11/2005 | Brewer et al. |
| 7,030,277 | B2 | 4/2006 | Groten et al. |
| 7,060,372 | B2 | 6/2006 | Fryd et al. |
| 7,071,362 | B2 | 7/2006 | Sugawara et al. |
| 7,160,524 | B2 | 1/2007 | Lederer et al. |
| 7,301,055 | B2 | 11/2007 | Hoffmockel et al. |
| 7,321,052 | B2 | 1/2008 | Miller et al. |
| 7,488,851 | B2 | 2/2009 | Rodrigues et al. |
| 7,498,451 | B2 | 3/2009 | Haderlein et al. |
| 7,534,922 | B2 | 5/2009 | Gorling et al. |
| 7,754,900 | B2 | 7/2010 | Siegert et al. |
| 8,785,697 | B2 | 7/2014 | Billodeaux et al. |
| 9,000,229 | B2 * | 4/2015 | Devon et al. ............ 568/678 |
| 9,056,313 | B2 * | 6/2015 | Devon et al. ............ 568/678 |
| 2003/0187281 | A1 | 10/2003 | Miller et al. |
| 2006/0129000 | A1 | 6/2006 | Goring et al. |
| 2008/0283384 | A1 | 11/2008 | Lang et al. |
| 2010/0048940 | A1 | 2/2010 | Tulchinsky et al. |
| 2010/0099894 | A1 | 4/2010 | Dubois et al. |
| 2010/0158780 | A1 | 6/2010 | Galligan et al. |
| 2010/0228065 | A1 | 9/2010 | Cheung et al. |
| 2010/0261936 | A1 | 10/2010 | Okumura et al. |
| 2010/0292491 | A1 | 11/2010 | Selifonov et al. |
| 2011/0034739 | A1 | 2/2011 | Stochniol et al. |
| 2011/0207969 | A1 | 8/2011 | Olken et al. |
| 2012/0121911 | A1 | 5/2012 | Mullen et al. |
| 2012/0330032 | A1 | 12/2012 | Terrill et al. |
| 2012/0330033 | A1 | 12/2012 | Terrill et al. |
| 2012/0330034 | A1 | 12/2012 | Billodeaux et al. |
| 2012/0330066 | A1 | 12/2012 | Devon et al. |
| 2012/0330067 | A1 | 12/2012 | Devon et al. |
| 2012/0330069 | A1 | 12/2012 | Billodeaux et al. |

FOREIGN PATENT DOCUMENTS

| | | |
|---|---|---|
| DE | 3328561 A1 | 2/1985 |
| DE | 238 232 A1 | 8/1986 |
| DE | 19648960 A1 | 5/1998 |
| DE | 10036423 A1 | 3/2001 |
| EP | 0 168 989 A1 | 1/1986 |
| EP | 0 169 666 B1 | 1/1986 |
| EP | 0 271 091 A1 | 6/1988 |
| EP | 0 312 659 A1 | 4/1989 |
| EP | 0499055 A2 | 8/1992 |
| EP | 0616994 A2 | 9/1994 |
| EP | 0624563 A1 | 11/1994 |
| EP | 0696564 A1 | 2/1996 |
| EP | 1 236 511 A1 | 9/2002 |
| FR | 2 906 246 A1 | 3/2008 |
| GB | 1020500 A | 2/1966 |
| GB | 1046608 A | 10/1966 |
| JP | 52073810 A | 6/1977 |
| JP | 56166186 A | 12/1981 |
| JP | 58198431 A | 11/1983 |
| JP | 5155878 A | 6/1993 |
| JP | 5271217 A | 10/1993 |
| JP | 6128184 A | 5/1994 |
| JP | 7-224055 A | 8/1995 |
| JP | 2001-031671 A | 2/2001 |
| JP | 2001072636 A | 3/2001 |
| JP | 4287546 B2 | 7/2009 |
| WO | WO 01/19763 A1 | 3/2001 |
| WO | WO 03/002547 A1 | 1/2003 |
| WO | WO 2010/027663 A1 | 3/2010 |

OTHER PUBLICATIONS

Hao et al. "Downstream processing of 1,3-propanediol fermentation broth" J. Chem. Technol. Biotechnol. 2006, 81, pp. 102-108.

Howard et al. "Hydrogenolysis of Ketals" J. Org. Chem., 1961 26(4), pp. 1026-1028.

Osman et al. "Cyclic Acetal Formation Between 2-Pyridinecarboxaldehyde and y-Hydroxy-a,b-Acetylenic Esters" Tetrahedron Lett. 2008, 49 (46) pp. 6550-6552.

Zajac et al. "Reaction of 2-Butynal Diethyl Acetal with Lithium Aluminum Hydride" J. Org. Chem., 1975 40(4), pp. 530-531.

Astle et al. "Catalysis with Cation-Exchange Resins, Preparation of 1,3 Dioxolanes and 1,3,6-Trioxocanes", Industrial and Engineering Chemistry, Apr. 1954, pp. 787-791.

Singh et al. "Production of Butyl Acetate by Catalytic Distillation. Theoretical and Experimental Studies" Ind. Eng. Chem. Res. 2005, 44, pp. 3042-3052.

Venimadhavan et al. "A Novel Distillate Policy for Batch Reactive Distillation with Application to the Production of Butyl Acetate" Ind. Eng. Chem. Res. 1999, 38, pp. 714-722.

Chadda et al. "Feasibility and Synthesis of Hybrid Reactive Distillation Systems" AIChE Journal, Dec. 2002, vol. 48, No. 12, pp. 2754-2768.

Sulzbacher et al., J. Am. Chem. Soc. 1948, 70(8), pp. 2827-2828.

Bronsted and Grove, J. Am. Chem. Soc. 1930, 52(4), pp. 1394-1403.

Van Duzee et al., J. Am. Chem. Soc. 1935, 57, p. 147.

Bonner et al., J. Am. Chem. Soc., Perkins Trans. 1981, pp. 1807-1810.

Tkachenko et al. "Research in the Field of Furan Acetal Compounds. XII. Features of the Vapor-Phase Hydrogenation of Disubstituted 1,3-Dioxolanes", Chemistry and Technology of Furan Compounds, 1985, pp. 59-64.

Public Dow literature, "Dow Technology Licensing—METEOR™ Ethylene Oxide/Glycol Process Technology," http://www.dow.com/licensing/offer/meteor.htm (downloaded and printed from the internet on Aug. 24, 2011).

Public Shell literature, "Factsheets: OMEGA and ethylene oxide/ ethylene glycol technology," http://www.shell.com/home/content/chemicals/aboutshell/media_centre/factsheets/omega/ (downloaded and printed from the internet on Aug. 24, 2011).

Public website at http://globalbiochemna.com/, Global BioChem Technology Group (GBT), Product Information, "About Us, and Glycols Project/Polyol Chemicals" (downloaded and printed from the internet on Aug. 24, 2011).

Public Dow literature, Dow Product Safety Assessment, "Ethylene Glycol Butyl Ether" (EGBE), at http://www.dow.com/productsafety, Product Safety Assessment Finder. (downloaded and printed from the internet on Aug. 24, 2011).

Kul'nevich et al., Khimiya Geterotsiklicheskikh Soyedinenii, No. 8, 1977, pp. 1026-1029.

Coelho, Antonio Carlos Vieira, et al.; "Surface Area, Crystal Morphology and Characterization of Transition Alumina Powders from a New Gibbsite Precursor"; Materials Research, vol. 10, No. 2, pp. 183-189, (2007), XP002683656.

Hudson, L. Keith, et al.; "Aluminum Oxide", Internet Citation XP-002596245, pp. 1-40, Jun. 15, 2000, URL: http://onlinelibrary.wiley.com/doi/10.

Luyben, William L., et al.; "Reactive Distillation Design and Control", John Wiley & Sons, 2008, p. 514-517.

Hibbert, H., et al.: Studies on the reactions relating to carbohydrates and polysaccharides. X. Synthesis and relative stability of cyclic acetals from 1, 2- and 1, 3-glycols; Journal of the American Chemistry Society, vol. 46, No. 5, 1924. pp. 1283-1290, XP002621973, cited in the application pp. 1286, 1287, "Experimental Part".

(56) References Cited

OTHER PUBLICATIONS

Stichlmair, Johann, et al.; "Reactive Distillation Processes"; Chemical Engineering Technology, 22 (1999) 2; pp. 95-103.
Notification of Transmittal of the International Search Report and the Written Opinion of the International Searching Authority dated Jun. 19, 2012 for International Application No. PCT/US2012/043085.
Notification of Transmittal of the International Search Report and the Written Opinion of the International Searching Authority dated Jun. 14, 2012 for International Application No. PCT/US2012/042378.
Notification of Transmittal of the International Search Report and the Written Opinion of the International Searching Authority dated Jun. 8, 2012 for International Application No. PCT/US2012/041459.
Notification of Transmittal of the International Search Report and the Written Opinion of the International Searching Authority dated Sep. 3, 2012 for International Application No. PCT/US2012/042458.
Notification of Transmittal of the International Search Report and the Written Opinion of the International Searching Authority dated Sep. 11, 2012 for International Application No. PCT/US2012/043071.
Notification of Transmittal of the International Search Report and the Written Opinion of the International Searching Authority dated Oct. 15, 2012 for International Application No. PCT/US2012/042453.
Notification of Transmittal of the International Search Report and the Written Opinion of the International Searching Authority dated Sep. 14, 2012 for International Application No. PCT/US2012/043093.
USPTO Office Action dated Nov. 9, 2012 for co-pending U.S. Appl. No. 13/168,374.
USPTO Office Action dated Nov. 26, 2012 for co-pending U.S. Appl. No. 13/168,229.
USPTO Office Action dated May 21, 2013 for co-pending U.S. Appl. No. 13/168,374.
USPTO Office Action dated Jul. 1, 2013 for co-pending U.S. Appl. No. 13/168,229.
USPTO Office Action dated Aug. 15, 2013 for co-pending U.S. Appl. No. 13/168,330.
USPTO Office Action dated Nov. 1, 2013 for co-pending U.S. Appl. No. 13/168,274.
USPTO Office Action dated Nov. 1, 2013 for co-pending U.S. Appl. No. 13/168,304.
USPTO Office Action dated Nov. 1, 2013 for co-pending U.S. Appl. No. 13/168,349.
USPTO Office Action dated Nov. 4, 2013 for co-pending U.S. Appl. No. 13/168,361.
USPTO Office Action dated Feb. 26, 2014 for co-pending U.S. Appl. No. 13/168,229.
USPTO Notice of Allowance dated Jun. 3, 2014 for co-pending U.S. Appl. No. 13/168,374.
USPTO Office Action dated Jun. 4, 2014 for co-pending U.S. Appl. No. 13/168,304.
USPTO Office Action dated Jun. 5, 2014 for co-pending U.S. Appl. No. 13/168,349.
USPTO Notice of Allowance dated Jun. 17, 2014 for co-pending U.S. Appl. No. 13/168,361.
USPTO Office Action dated Jul. 2, 2014 for co-pending U.S. Appl. No. 13/168,274.
USPTO Notice of Allowance dated Jul. 7, 2014 for co-pending U.S. Appl. No. 13/168,374.
USPTO Notice of Allowance dated Jul. 9, 2014 for co-pending U.S. Appl. No. 13/168,330.
Copending U.S. Appl. No. 14/337,544, filed Jul. 22, 2014; Daniel Latham Terrill et al.
USPTO Notice of Allowance dated Aug. 4, 2014 for co-pending U.S. Appl. No. 13/168,229.
Copending U.S. Appl. No. 14/459,875, filed Aug. 14, 2014; Damon Ray Billodeaux et al.
USPTO Notice of Allowance dated Apr. 21, 2015 for co-pending U.S. Appl. No. 13/168,349.
USPTO Office Action dated May 5, 2015 for co-pending U.S. Appl. No. 14/459,875.
USPTO Office Action dated May 7, 2015 for co-pending U.S. Appl. No. 14/337,544.
USPTO Office Action dated Nov. 18, 2015 for co-pending U.S. Appl. No. 14/337,544.
USPTO Office Action dated Dec. 11, 2015 for co-pending U.S. Appl. No. 13/168,304.
USPTO Office Action dated Jan. 29, 2016 for co-pending U.S. Appl. No. 14/605,067.
V.I. Stenberg et al., "Catalytic Dehydrator. A Simplified Isolation Procedure for Acetals and Ketals," J. Org. Chem., vol. 39, pp. 2815-2816 (1974).
USPTO Office Action dated Jun. 25, 2015 for co-pending U.S. Appl. No. 13/168,304.
USPTO Office Action dated Oct. 21, 2015 for co-pending U.S. Appl. No. 14/459,875.

* cited by examiner

NICKEL MODIFIED CATALYST FOR THE PRODUCTION OF HYDROXY ETHER HYDROCARBONS BY VAPOR PHASE HYDROGENOLYSIS OF CYCLIC ACETALS AND KETALS

1. CROSS-REFERENCES TO RELATED APPLICATIONS

This application is a continuation of U.S. application Ser. No. 13/168,361 filed on Jun. 24, 2011.

2. FIELD OF THE INVENTION

The invention relates to a catalyst composition and to the production of hydroxy ether hydrocarbons from the hydrogenolysis of cyclic acetals or cyclic ketals in the vapor phase using the catalyst composition.

3. BACKGROUND OF THE INVENTION

Acetals and ketals are readily obtained by the reaction of aldehyde or ketone hydrocarbons and polyhydroxy hydrocarbons by many methods well known in the art. There are many references to the efficient preparation of these materials. It is desirable to prepare 2-alkoxy-ethanol compounds, such as 2-n-butoxyethanol and 2-n-propoxyethanol without the requirement of using ethylene oxide as the reactant. It is also desirable to have a process which is robust enough to prepare other hydroxy ether compounds without the requirement of using other highly reactive epoxy compounds and similar materials such as propylene oxide, 1,2-epoxybutane, glycidol (2,3-epoxy-1-propanol) and trimethylene oxide. It is also desirable to prepare hydroxy ether compounds in high selectivity without requiring alkylating agents such as alkyl bromides, chlorides and sulfates in their reaction with polyhydroxy compounds in a Williamson ether synthesis with the concurrent production of waste salts.

The classes of compounds known as hydroxy ether hydrocarbons have great value as solvents and dispersants for latex paints and other coatings. They also have value as components of industrial and consumer cleaning solutions and surfactants and raw materials for the preparation of polyurethane materials. The large bulk of this class of compounds that are commercially available are generally known as "E-series" and "P-series" solvents. The "E-series" solvents are prepared by the reaction of ethylene oxide (EO) with corresponding alcohols to form the "E-series" products. Conversely, the "P-series" of solvents are prepared by the reaction of propylene oxide (PO) with corresponding alcohols to form similar materials. This technology has a number of concerns and difficulties. First, ethylene oxide and propylene oxide are hazardous materials. Likewise, the nature of the reaction of an alcohol with highly reactive epoxides generates relatively low selectivity for desirable mono addition of EO or PO to the alcohol resulting in di-, tri and poly-EO or PO addition products in significant amounts. Third, the technology of mono ethylene glycol (MEG) production is moving away from the traditional isolation of ethylene oxide and subsequent reaction with water toward more efficient methods to prepare MEG in higher yield that use other technology, such as ethylene carbonate and direct water quenching of crude EO reactor product. These newer technologies remove a ready source of on-site EO for the production of E-series products. Fourthly, historically, a large capital intensive EO/MEG facility needs to be located in close proximity to the alcohol production facility to be efficient and avoid the risk of having to transport EO over long distances. In the case of "P-series" products, a propylene oxide unit also has to be conveniently located. The traditional preparation of PO involves the co-product formation of precursor materials leading to final products such as styrene and MTBE. Other methods to make PO have been developed, as for example, by the use of expensive hydrogen peroxide. The use of PO to make P-series materials thus has cost concerns.

Dioxolane compounds are characterized by having a five-membered ring with oxygen atoms in the 1 and 3 positions. Other materials based on renewable materials can also be used to prepare acetal compounds by known reactions with aldehydes, including glycerin, 1,3-propanediol and sugar-derived polyols such as mannitol, erythritol, 1,2- and 2,3-butanediol, and the like. In some of these other examples a class of acetal compound having a six-membered ring with oxygen atoms in the 1 and 3 positions known as 1,3-dioxanes can be prepared. Ketals may also be prepared by the reaction of ketone hydrocarbons with the above poly hydroxyl hydrocarbons in a similar manner to that of the preparation of acetals.

Previous work has been disclosed in the literature that discusses the hydrogenolysis of acetals, both cyclic and open to produce ether type hydrocarbons. In the case of 1,3-dioxolane acetal compounds, work has been disclosed that describes the preparation of valuable 2-alkoxy ethanol compounds. This chemical transformation is carried out by the cleavage of the oxygen-carbon bond attached to the carbon in the 2-position of the ring with hydrogen using a noble metal catalyst. The focus of that work has been on the liquid-phase hydrogenolysis of acetals in a solvent that is typically the diol moiety used to prepare the cyclic acetal. The art teaches the importance of having a large excess of this diol solvent present during the hydrogenolysis reaction to prevent the formation of significant amounts of undesired co-product, namely a diether.

U.S. Pat. No. 4,479,017 discusses the desire to generate ether compounds in high selectivity and yield by employing a palladium catalyst on a carbon carrier support in the absence of an added acid promoter compound. U.S. Pat. No. 4,484,009 discloses the product of monoethers of monoethylene glycol by hydrogenolysis of an acetal with a co-catalytic system of a palladium catalyst in combination with an acidic phosphorus promoter compound and ethylene glycol. In both instances, the reactions were conducted in the liquid phase. There remains a need to provide suitable catalyst systems that will generate hydroxy ether hydrocarbons in high selectivity in a vapor phase hydrogenolysis process.

4. SUMMARY OF THE INVENTION

There is now provided a process comprising contacting hydrogen with a cyclic compound comprising a cyclic acetal or a cyclic ketal in the vapor phase in the presence of a catalyst composition to produce a hydroxy ether hydrocarbon, wherein the catalyst composition comprises an aluminum oxide support containing or on which is deposited:
  i. palladium present in an amount of at least 0.8 wt % and up to 5 wt % based on the weight of the catalyst composition, and
  ii. nickel present in an amount of 500 ppmw up to 3000 ppmw.
  There is also provided a process of:
  (a) feeding hydrogen and the cyclic compound composition to a reaction zone within a reaction vessel, and
  (b) conducting a reaction in the reaction zone comprising contacting hydrogen with at least a portion of the cyclic compound composition in the presence a catalyst composition in the reaction zone under reaction zone conditions above the dew point of the cyclic compound composition to produce hydroxy ether hydrocarbons, fed to the reaction zone, and (c) withdrawing a product stream from the reaction zone comprising hydroxy ether hydrocarbons, hydrogen, and if present any unreacted cyclic compounds;

wherein the catalyst composition comprises an aluminum oxide support containing or on which is deposited:

i. palladium present in an amount of at least 0.8 wt % and up to 5 wt % based on the weight of the catalyst composition, and ii. nickel present in an amount of 500 ppmw up to 3000 ppmw based on the weight of the catalyst composition.

There is also now provided a process comprising contacting cyclic compounds in the vapor phase with hydrogen in the presence of this catalyst composition and in a reaction zone to produce a vapor hydroxy ether hydrocarbon, wherein said cyclic compounds comprise cyclic acetals, cyclic ketals, or a combination thereof.

5. DETAILED DESCRIPTION OF THE INVENTION

As used herein, "cyclic compounds" includes cyclic acetal compounds, cyclic ketal compounds, and combinations thereof. The term "within" includes the end points of a range.

We have surprisingly found that an efficient hydrogenolysis reaction can be carried out to transform cyclic compounds, such as 1,3-dioxolane compounds and 1,3-dioxane classes of compounds, with high selectivity in a vapor phase reaction using catalysts having a combination of features. Improving the selectivity to the production of the desired hydroxy ether mono-hydrocarbon is the criteria of choice because the unconverted compounds can be recycled for conversion to the desired hydroxy ether hydrocarbon, whereas catalysts with high activity but low selectivity are problematic because the cyclic acetals can be converted to by-products which have no possibility of further conversion to desired hydroxy ether mono-hydrocarbons.

We have found that a particular catalyst is highly selective for obtaining the desired hydroxyl ether hydrocarbon product, often in greater than 90% molar selectivity from the converted acetal feed material. The catalyst compositions used in the process of the invention is an aluminum oxide support containing or on which is deposited:

i. palladium present in an amount of at least 0.8 wt % and up to 5 wt % based on the weight of the catalyst composition, and ii. nickel present in an amount of 100 ppmw up to 5000 ppmw.

Aluminum oxide has many phases. Suitable phases include alpha, gamma, theta, and delta. For some catalyst compositions of the invention, the phases include the alpha and gamma phases. Each of these phases and their characterization are well known. For example, the α-alumina (alpha) phase has a hexagonal crystal structure which is the most thermodynamically stable form. γ-alumina (gamma) typically has a cubic crystal structure which is also stable at the operating temperatures of the invention. θ-alumina (theta) crystal structure can be characterized as typically having a monoclinic crystal structure, although the crystal structure can vary depending on the calcining temperature. The crystal structure of these forms are known and described in, for example, Kirk Othmer Encyclopedia of Chemical Technology, Volume 2, pages 302-317 (1992).

An α-aluminum oxide support desirably contains more than 95% of its crystal phases in the alpha phase. These ultrapure alpha phase aluminum oxide supports are desirable. Such high purity supports contain at least 97%, or at least 98%, or at least 99% of their phases in the alpha phase. α-aluminum oxide supports that have less than 90% alpha phase content often also contain high amounts of silicon oxide. Alumina supports with high contents of silicon oxide impact the selectivity of the catalyst toward the production of the desired hydroxy ether mono-hydrocarbon. γ-alumina supports have a gamma phase content of at least 95%, or at least 96%, or at least 97%, or at least 98%, or at least 99%. θ-alumina supports have a theta phase content of at least 95%, or at least 96%, or at least 97%, or at least 98%, or at least 99%. Like the alpha phase aluminum oxide supports, silicon oxides such as silicon dioxide poison the selectivity of the catalyst toward the production of hydroxy ether mono-hydrocarbon compounds.

The BET surface area (determined by the BET method by nitrogen adsorption to DIN 9277) of the aluminum oxide support is at least 0.1 m2/g, or at least 0.2 m2/g, or at least 0.5 m2/g. or at least 1 m2/g. or at least 2 m2/g. or at least 3 m2/g and up to 350 m2/g, or less than 300 m2/g, and at least 100 m2/g, or at least 150 m2/g, or at least 200 m2/g.

Aluminum oxide supports with a low weight percentage of palladium loading generally yield catalysts that reduce the formation of byproducts such as diether compounds, ester compounds and other by-products that result from unselective reactions upon the cyclic compound feed and by secondary decomposition of liberated ethylene glycol, a co-product of diether formation. Surprisingly, the catalyst composition of the invention having high palladium loadings were highly selective to the production of the desired hydroxy ether hydrocarbons. The catalyst composition used in this invention has a high loading of palladium. Suitable palladium metal catalyst loadings for the catalyst used in the invention are at least 0.8 wt %, or at least 0.9 wt %, or at least 1.0 wt %, or more than 1.0 wt %, or at least 1.05 wt %, or at least 1.1 wt %, or at least 1.2 wt %, or at least 1.3 wt %, or at least 1.4 wt %, or at least 1.5 wt %, and up to or less than 5.0 wt %, or up to 3.0 wt %, or up to 2.0 wt %, or up to 1.5 wt %

Palladium can be loaded onto the supports by any conventional means. Palladium can be added as a metal or as a compound, such as palladium chloride, palladium chloride dihydrate, palladium bromide, palladium iodide, palladium oxide, or an organic palladium salt or complex such as palladium formate, palladium acetate, palladium butyrate and palladium acetylacetonate.

The catalyst compositions of the invention desirably have a low silicon dioxide content to improve the selectivity and yield to the product of hydroxy ether mono-hydrocarbon compounds. The supports for the catalysts may have a $SiO_2$ content of no more than 1.0 wt %, or less than 0.5 wt %, or less than 0.3 wt %, or no more than 0.2 wt %, or no more than 0.1 wt %. Those with low contents of silicon dioxide are effective at increasing selectivity.

The catalyst composition used in the process of the invention is doped with nickel. The use of nickel in certain amounts in combination with high loadings of palladium will increase the selectivity of converted acetal into desired products, even though high loadings of palladium are thought to be highly active but poorly selective. Nickel deposited onto the catalyst support may have an oxidation state of zero or other than zero. Suitable salts of nickel include organic anions, such as C1-C8 carboxylates and halides such as acetate, chloride and fluoride, bromides, nitrates, carbonates, sulphates, sulfides, hydroxides, ammonium nickel salts, and the like. Specific examples of such modifiers used to dope the supports include ammonium nickel(II) sulfate, bis(ethylenediamine)nickel(II) chloride, hexaamminenickel(II) iodide, nickel carbonate, nickel(II) acetate, nickel(II) bromide 2-methoxyethyl ether, nickel(II) bromide, nickel(II) bromide ethylene glycol dimethyl ether complex, nickel(II) carbonate hydroxide, nickel (II) chloride, nickel(II) cyclohexanebutyrate, nickel(II) fluoride, nickel(II) hydroxide, nickel(II) iodide, nickel(II) molybdate, nickel(II) nitrate, nickel(II) oxalate, nickel(II) perchlorate, nickel(II) sulfamate, nickel(II) sulfate, potassium nickel(IV) paraperiodate, potassium tetracyanonickelate(II) potassium tetracyanonickelate(II) hydrate, nickel (II) oxide, bis(cyclcooctadiene)nickel, and nickel tetracarbonyl, and the like.

The amount of nickel on the alumina support is sufficient to obtain improved selectivity over the same catalyst without nickel while obtaining an acceptable drop in activity. A drop in activity is acceptable because with high selectivity, unconverted compounds can be recycled for additional passes to obtain the desired hydroxy either monohydrocarbon compounds.

Suitable amounts of nickel are at least 100 ppmw, or at least 250 ppmw, or at least 500 ppmw, or at least 700 ppmw, or at least 900 ppmw, or at least 1000 ppmw, and up to 5000 ppmw, or up to 4000 ppmw, or up to 3000 ppmw, or up to 2500 ppmw, or up to 2000 ppmw, or up to 1750 ppmw, or up to 1500 ppmw, or up to 1250 ppmw.

Additional examples are amounts in a range of 100-5000, or 100-4000, or 100-3000, or 250-3000, or 250-2500, or 250-2000, or 250-1500, or 250-1250, or 500-3000, or 500-2500, or 500-2000, or 500-1500, or 500-1250, each in ppmw, based on the weight of the catalyst composition.

With some palladium catalysts on alumina supports, the addition of alkali or alkaline earth metal dopants have enhanced the selectivity of the catalyst toward the production of hydroxy ether mono-hydrocarbons. The addition of alkali metals to this palladium catalyst on alumina does not appear to enhance selectivity and in some circumstances, decreases selectivity. In addition, the activity of the catalyst is depressed to a level below that of industrial relevance. Thus, in a preferred aspect of the invention, the catalyst composition is free of alkali metal compounds present in significant quantities, that is, in amount exceeding 50 ppm, or in amounts exceeding 40 ppmw, or in amounts exceeding 30 ppmw, or in amounts exceeding 20 ppmw, or in amounts exceeding 10 ppmw, or in amounts exceeding 5 ppmw. In another embodiment, the catalyst composition is also free of alkaline earth metals in the same quantities.

The catalyst composition used in the process of the invention provide a selectivity to the production of hydroxy ether mono-hydrocarbons to a level of at least 80%, or at least 82%, or at least 84%, or at least 86%, or at least 88%, or at least 90%, or at least 92%, or at least 94%, or at least 95%. The conversion rates from the cyclic compounds to any and all converted reaction products is desirably at least 65%, or at least 70%, or at least 75%, or at least 80%, or at least 90%, or at least 92%, or at least 94%, or at least 95%. By avoiding a large drop in conversion, the production rate remains acceptable.

The hydroxy ether mono-hydrocarbons have both (i) at least one ether linkage and (ii) at least one hydroxyl group, and in addition, are those compounds in which the reaction product of cyclic acetal or cyclic ketal with one or more moles of hydrogen has not reacted any further with other cyclic acetals or cyclic ketals or other reaction products of cyclic acetals and cyclic ketals and hydrogen, and has not been subjected to a decrease in its molecular weight due to chain scission. If the cyclic acetal or ketal compound fed to the reaction zone contains 2 or more ether linkages to start, but does not react with any other cyclic acetal or cyclic ketal compounds or any other reaction products of hydrogen with cyclic acetals or cyclic ketals, it is deemed a hydroxy ether mono-hydrocarbon even though more than one ether linkage is present. This is because the reaction product of hydrogen and the cyclic acetal or cyclic ketal having multiple ether linkages has not reacted any further with other cyclic acetals or with any other reaction products of hydrogen and cyclic acetals or cyclic ketals.

The catalysts of the invention also are effective to suppress the formation of diether by-product compounds. It is advantageous to use a catalyst composition that, even though a significant improvement in selectivity is not observed, nevertheless results in the formation of fewer diether by-products. A product stream composition from a vapor phase hydrogenolysis of cyclic hydrocarbons that contains up to 5 wt % of diether compound co-products, or up to 4 wt %, or up to 3 wt %, or up to 2 wt %, or up to 1 wt % are also suitable.

The aluminum oxide supports may be obtained from natural sources or synthesized, such as by calcination of aluminum hydroxide.

The shape of the solid catalysts are not particularly limited but should be of a shape and size and robust enough to resist breaking in a catalyst bed. Spherical, star, and trilobal shapes are suitable for use in the invention.

The average particle sizes of the catalysts are not particularly limited. Shapes can be selected to provide efficient mass transfer. Suitable average particle sizes range from 0.1 mm to 8 mm, with 1 mm to 6 mm well suited in the practice of the invention.

The average pore size and pore volume of the supports is not particularly limited. Consideration is given for having pore sizes and pore density to support the palladium metal and provide active sites for the conversion of cyclic compounds to the hydroxy ether mono-hydrocarbon compounds. Typical average pore sizes range from 30 Å to 300 Å, or 60 Å to 200 Å, and typical pore volumes range from 0.2 cc/g to 1.0 cc/g, or 0.3 cc/g to 0.8 cc/g.

In the process of the invention, cyclic compounds in a cyclic compound composition are contacted with hydrogen in the vapor phase to produce hydroxy ether hydrocarbons. The cyclic compounds are in the vapor phase at least in the reaction zone and desirably also fed to the reaction zone in the vapor phase. For example, one may hydrogenate the cyclic compounds by:

(a) feeding hydrogen and a cyclic compound composition comprising cyclic compounds, and preferably a cyclic compound vapor composition, to a reaction zone within a reaction vessel, and (b) contacting at least a portion of the cyclic compound composition with hydrogen in the reaction zone under reaction zone conditions above the dew point of the cyclic compound composition fed to the reaction zone to produce hydroxy ether compounds in the reaction zone, and (c) withdrawing a product stream from the reaction zone comprising hydroxy ether hydrocarbons, hydrogen, and if present any unreacted cyclic compounds.

The cyclic compounds can be contacted with hydrogen in a reaction zone over a noble metal catalyst advantageously in the absence of a liquid, such as a solvent like ethylene glycol, in the reaction zone during the hydrogenolysis reaction. Also, advantageously, the noble metal catalyst does not need to be separated from the product stream effluent because the reaction proceeds in the vapor phase over a heterogeneous catalyst bed, preferably a fixed bed.

The cyclic compound composition of the invention contains cyclic compounds. The cyclic compounds that are contacted with hydrogen in the process of the invention are those having a cyclic acetal or ketal moiety. The cyclic acetal moiety produced in the process of the invention has two oxygen atoms single bonded to the same carbon atom in the ring structure. Examples include cyclic compounds having 1,3-dioxolane moieties and dioxane moieties (especially 1,3-dioxane moieties), as well as those having larger rings with oxygen atoms in the 1,3 position.

In one embodiment, the cyclic compound(s) may be represented by the general formula:

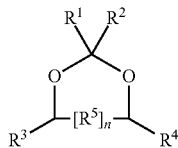

wherein $R^1$, $R^2$, $R^3$, and $R^4$ are independently H; an branched or un-branched $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cylcoalkyl, or a $C_3$-$C_{50}$ carboxylate ester; and wherein the alkyl, alkenyl, aryl, and cycloalkyl groups of $R^1$, $R^2$, $R^3$, and $R^4$ are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol;

and any one or both of $R^3$ and $R^4$ are optionally independently a hydroxyl, halogen, dialkylamino, amine, aldehyde, ketone, carboxylic acid, ester, ether, alkynyl, dialkylamide, anhydride, carbonate, epoxide, lactone, lactam, phosphine, silyl, thioether, thiol, or phenol;

and wherein $R^1$ and $R^2$ are not both H;

and $R^1$ and $R^2$ optionally together form a cycloalkyl having 3-12 carbon atoms;

and wherein $R^5$ is branched or unbranched, substituted or unsubstituted, divalent alkyl or divalent alkenyl group each having 1 to 8 carbon atoms and optionally containing 1, 2, or 3 oxygen atoms in the alkyl or alkenyl group;

and wherein n is an integer selected from 0 or 1.

$R^1$, $R^2$, $R^3$, and $R^4$ may independently be H, or a branched or un-branched $C_1$-$C_6$ alkyl group. Or, $R^1$, $R^2$, $R^3$, and $R^4$ may independently be H, or a branched or un-branched $C_1$-$C_4$ alkyl group. $R^1$ may be a branched or unbranched $C_1$-$C_6$ alkyl group while $R^2$ is a hydrogen atom.

$R^5$ may be a branched or unbranched divalent alkyl group having 1 to 6, or 1 to 4, or 1 to 3, or 1 to 2 carbon atoms.

Examples of cyclic acetals include 2-propyl-1,3-dioxolane, 2-propyl-1,3-dioxane, 2-ethyl-1,3-dioxolane, 2-ethyl-1,3-dioxane, 2-methyl-1,3-dioxolane, 2-methyl-1,3-dioxane, 2-propyl-4-methyl-1,3-dioxane, 5,5-dimethyl-2-propyl-1,3-dioxane, 5,5-dimethyl-2-ethyl-1,3-dioxane, 4-hydroxymethyl-2-propyl-1,3-dioxolane, 4-hydroxymethyl-2-propyl-1,3-dioxane, 2-ethyl-1,3-dioxepane, 2-ethyl-1,3,6-trioxocane.

As to substituents, in one embodiment, $R^3$ or $R^4$ is a hydroxyl group.

In the case one desires to use a cyclic acetal compound as a starting material, one of $R^1$ or $R^2$ is a hydrogen atom. $R^1$ and $R^2$ may independently be H, or a branched or un-branched $C_1$-$C_6$ alkyl group. Or, $R^1$ and $R^2$ may independently be H, or a branched or un-branched $C_1$-$C_4$ alkyl group. $R^1$ may be a branched or unbranched $C_1$-$C_6$ alkyl group while $R^2$ is a hydrogen atom. Particularly useful cyclic acetals for this invention leading to useful materials of commerce include 1,3-dioxolanes having $R^1$ being an alkyl group that can lead to "E-series" type solvents. Likewise, 1,3-dioxolanes having $R^1$ being an alkyl group and $R^3$ being a methyl group can lead to "P-series" type solvents.

In the case one desires to start with a cyclic ketal compound as the starting material, then neither $R^1$ nor $R^2$ are hydrogen atoms. $R^1$ and $R^2$ may independently be a branched or un-branched $C_1$-$C_6$ alkyl group. Or, $R^1$ and $R^2$ may independently be a branched or un-branched $C_1$-$C_4$ alkyl group. Other potentially useful acetals that make use of 1,3-propylene glycol and glycerin in their preparation would include 1,3-dioxane acetals having $R^1$ being an alkyl group and 1,3-dioxane acetals having $R^1$ being an alkyl group and $R^4$ being a hydroxyl group. A variation of the glycerin acetals that have potentially useful derivatives would be 1,3-dioxolane acetals having $R^1$ being an alkyl group and $R^3$ being a hydroxymethyl group.

Examples of cyclic acetals that have 1,3-dioxolane moieties include 2-propyl-1,3-dioxolane, 2-propyl-1,3-dioxolane, 2-ethyl-1,3-dioxolane, 2-methyl-1,3-dioxolane, 4-hydroxymethyl-2-propyl-1,3-dioxolane.

Examples of cyclic acetals that have 1,3-dioxane moieties include 2-propyl-1,3-dioxane, 2-ethyl-1,3-dioxane, 2-methyl-1,3-dixoane, 2-propyl-4-methyl-1,3-dioxane, 5,5-dimethyl-2-propyl-1,3-dioxane, 5,5-dimethyl-2-ethyl-1,3-dioxane, and 4-hydroxymethyl-2-propyl-1,3-dioxane.

Examples of cyclic ketals that can be utilized in the present invention include, but are not limited to, 2,2-dimethyl-1,3-dioxolane, 2,2-dimethyl-1,3-dioxane, 2,2,4-trimethyl-1,3-dioxolane, 2,2-dimethyl-1,3-dioxepane, 2,2-dimethyl-1,3,6-trioxocane, 4-methanol-2,2-dimethyl-1,3-dioxolane, 2,2-dimethyl-1,3-dioxan-5-ol, 2,2,5,5-tetramethyl-1,3-dioxane, 2-ethyl-2-methyl-1,3-dioxolane, 2-ethyl-2-methyl-1,3-dioxane, 2-ethyl-2,4-dimethyl-1,3-dioxane, 2-ethyl-2-methyl-1,3-dioxepane, 2-ethyl-2-methyl-1,3,6-trioxocane, 2-ethyl-2,5,5-trimethyl-1,3-dioxane, 4-methanol-2-ethyl-2-methyl-1,3-dioxolane, 2-ethyl-2-methyl-1,3-dioxan-5-ol, 2-methyl-2-propyl-1,3-dioxolane, 2-methyl-2-propyl-1,3-dioxane, 2,4-dimethyl-2-propyl-1,3-dioxane, 2-methyl-2-propyl-1,3-dioxepane, 2-methyl-2-propyl-1,3,6-trioxocane, 2,5,5-trimethyl-2-propyl-1,3-dioxane, 4-methanol-2-propyl-1,3-dioxolane, 2-methyl-2-propyl-1,3-dioxan-5-ol, 2-methyl-2-pentyl-1,3-dioxolane, 2-methyl-2-pentyl-1,3-dioxane, 2,4-dimethyl-2-pentyl-1,3-dioxane, 2-methyl-2-pentyl-1,3-dioxepane, 2-methyl-2-pentyl-1,3,6-trioxocane, 2,5,5-trimethyl-2-pentyl-1,3-dioxane, 4-methanol-2-methyl-2-pentyl-1,3-dioxolane, and 2-methyl-2-pentyl-1,3-dioxan-5-ol.

The cyclic acetals and ketals are prepared by reacting a polyhydroxyl compound with a carbonyl functional compound that is either an aldehyde or a ketone, in the present of an acid catalyst.

The cyclic acetals and ketals are prepared by reacting a polyhydroxyl compound with a carbonyl functional compound that is either an aldehyde or a ketone, in the present of an acid catalyst.

The polyhydroxyl compounds have at least two hydroxyl (—OH) functionalities. The polyhydroxyl compounds may contain ether or ester linkages in the longest carbon chain.

Suitable polyhydroxyl compounds for the present invention include, but are not limited to ethylene glycol, 1,2-propanediol, 1,3-propanediol, 1,4-butanediol, 1,3-butanediol, 1,2-butanediol, 1,2-pentanediol, 2,4-pentandiol, 2,2-dimethyl-1,3-propanediol, diethyleneglycol, and triethyleneglycol, glycerin, trimethylolpropane, xylitol, arabitol, 1,2- or 1,3cyclopentanediol, 1,2- or 1,3-cyclohexanediol, and 2,3-norbornanediol.

The carbonyl compounds contain at least one carbonyl functionality. In the present invention, any carbonyl compound may be used.

For example, the carbonyl compound is represented by the formula:

in which $R^1$ and $R^2$ are independently H, $C_1$-$C_{50}$ alkyl, $C_2$-$C_{50}$ alkenyl, aryl-$C_1$-$C_{50}$ alkyl, aryl-$C_2$-$C_{50}$ alkenyl-, or $C_3$-$C_{12}$ cylcoalkyl, and wherein the alkyl, alkenyl, aryl, and cycloalkyl groups of $R^1$ are optionally saturated or unsaturated, and branched or unbranched or substituted or unsubstituted with 1, 2, or 3 groups comprising —OH, halogen, dialkylamino, $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, aryl, phenol, or combinations thereof. $R^1$ and $R^2$ optionally together form a cycloalkyl having 3-12 carbon atoms;

When one of $R^1$ and $R^2$ is hydrogen, the carbonyl compound is an aldehyde compound. The aldehyde compound may have, if desired, at least one aldehyde functional group wherein the aldehyde carbon atom is bonded to a (i) branched or unbranched $C_1$-$C_9$ alkyl group or (ii) an aryl or alicyclic group which is optionally substituted with a branched or unbranched $C_1$-$C_9$ alkyl group.

Examples of an aldehyde compounds include, but are not limited to, formaldehyde, benzaldehyde, acetaldehyde, propionaldehyde, butyraldehyde, isobutyraldehyde, pentaldehyde, 2-methylbutyraldehyde, 3-methylbutyraldehyde, n-pentanal, isopentanal, hexaldehyde, heptaldehyde, 2-ethylhexaldehyde, octanal, nonanal, n-decanal, 2-methylundecanal, lauryl aldehyde, myristyl aldehyde, cetyl aldehyde, stearyl aldehyde, behenyl aldehyde, glutaraldehyde, acrolein, crotonaldehyde, oleyl aldehyde, linoleyl aldehyde, linolenyl aldehyde, erucyl aldehyde, cinnamaldehyde, 1,3-cyclohexanedicarboxaldehyde, 1,4-cyclohexanedicarboxaldehyde, and combinations thereof.

Preferably, the aldehyde compound is 2-ethylhexaldehyde or an aliphatic aldehyde compound wherein the aldehyde carbon atom is bonded to a branched or unbranched $C_1$-$C_5$ alkyl group (for a total of 2-6 carbon atoms). Examples of the latter compounds include acetaldehyde, propionaldehyde, butyraldehyde, isobutyraldehyde, pentaldehyde, 2-methylbutyraldehyde, 3-methylbutyraldehyde, hexaldehyde, benzaldehyde, 2-ethylhexaldehyde, octanal, nonanal.

When neither $R^1$ nor $R^2$ is hydrogen, the carbonyl compound is a ketone. Examples of suitable ketone compounds include, but are not limited to, acetone, methyl isobutyl ketone (2-butanone), methyl ethyl ketone, methyl propyl ketone (2-pentanone), methyl isopropyl ketone (3-methyl-2-butanone), methyl isobutyl ketone (4-methyl-2-pentanone), 2-hexanone, cyclohexanone, 2-heptanone (methyl amyl ketone), 4-heptanone, and 2-octonone.

The starting feed materials used in the process of the invention comprise cyclic acetal compounds or cyclic ketal compound or combinations thereof. The process of the invention is a vapor phase reaction conducted at an elevated pressure. Therefore, the feed materials selected should be sufficiently volatile to enter the reaction vessel in a gaseous state as a gaseous feed stream. Accordingly, the feed materials must have a pure liquid vapor pressure of at least 1 mm Hg (0.133 kPa) (at the reaction temperature). To obtain better reaction rates, it is desired to select a feed material that has a vapor pressure in excess of 10 mm Hg (1.33 kPa).

For example, feed material compounds with relatively high boiling points like a cyclic acetal or ketal compound can be selected with high boiling points (at 1 atm) in excess of 200° C. or even at least 250° C. (523 degrees K) because those same compounds may have practical vapor pressures of in excess of 50 mm Hg or at least 70 mm Hg (9.33 kPa) at typical hydrogenolysis reaction temperatures (at least 150° C., or at least 180° C. or at least 190° C. or at least 200° C.) in the reaction vessel.

The process has the ability to be operated at a wide range of reaction temperature conditions. Suitable reaction temperatures (reactor set points) range from at least 100° C., or at least 130° C., or at least 150° C., or at least 170° C., or at least 180° C., or at least 190° C., or at least 200° C., or at least 210° C., or at least 220° C., and up to 300° C., or up to 275° C., or up to 250° C., or up to 240° C., or up to 230° C., or up to 220° C., or up to 210° C., or up to 200° C.

The favored temperature range for the practice of the invention is at least 150° C. because reaction rates increase at higher temperatures and up to about 250° C. Temperatures in excess of 250° C. start to suffer from excessive side product reactions. Suitable ranges include 190° to 250° C., or 200° to 230° C.

The efficiency of the process is increased if the operating reaction conditions are at temperatures above the dew point of the cyclic compound composition in the gaseous feed stream at reaction pressure. In another embodiment, the operating reaction conditions are at a temperature above the dew point of both the cyclic compound composition and the reaction products of the cyclic acetals in the gaseous product stream.

Dew point is defined as the temperature and pressure at which liquid condensation begins to take place for a gaseous mixture having a condensable material. See Dictionary of Scientific and Technical Terms published by McGraw-Hill, Fifth Edition, 1994. In practice, dew point is controlled by a combination of factors. The first factor is the actual vapor pressure of a pure liquid as a function of temperature. Increasing temperature increases the vapor pressure of a pure liquid thereby making it less likely to condense at higher temperature. Cyclic acetals and ketals behave in this manner. Lowering the temperature also lowers the vapor pressure of the liquid. Thus, operating the reaction at lower temperatures will require lowering the pressure in the reaction vessel to prevent the cyclic acetals from dropping below their dew point. It is desirable to conduct the hydrogenolysis at elevated temperatures in order to keep materials from condensing into a liquid phase at reaction conditions.

The second factor that keeps the cyclic compounds in the gaseous state and prevents them from dropping below their dew points is to keep the reactor absolute pressure low enough to keep the actual partial pressure of the component cyclic acetals above the dew point in the gaseous feed. The partial pressure of the cyclic acetals is related to the vapor pressure of the pure compounds at reaction temperature. Partial pressure (PP) of a given component "b" is defined: P(absolute)×(mole fraction of b in the mixture). Mole fraction is the portion of moles of the component in the total moles of a mixture. The partial vapor pressures of organic materials in this invention at reaction pressure and temperature must remain below the vapor pressure of the pure materials at that reaction temperature to avoid condensation. In essence, lowering reactor absolute pressure of a given mole fraction of reactant cyclic acetal in the feed will thereby lower the partial pressure of the reactant cyclic acetal. The vapor pressures of pure materials may be obtained by normal calculations with established physical constants or obtained from vapor pressure tables. For example one such method of vapor pressure calculation for the pure compound 2-n-propyl-1,3-dioxolane (PDX) would be: vapor pressure of PDX in mm Hg=10**((−0.2185×(A/K)+B) where A=10183.9; K=Temperature of the PDX in degrees Kelvin; and B=+8.363358. Thus the vapor pressure of pure PDX would be about 4560 mm Hg (607.95 kPa) at 200 degrees Celsius (473 degrees K).

Without being bound to a theory, not having liquid condensation on the surface of the supported noble metal catalyst facilitates the transfer of gaseous hydrogen into the catalytic cycle. In addition, the lack of liquid organic materials on the surface of the catalyst reduces the ability for product reaction leading to unwanted byproducts. Indeed, we have also found that decreased residence time on the catalyst increases the selectivity to the desired hydroxyether hydrocarbon product without significantly affecting the reaction rate of the catalytic process. It is most desirable to hold the residence time of materials on the catalyst surface at between 0.25 and 1.5 seconds.

The hydrogenolysis reaction uses hydrogen as both a gaseous feed medium and reactant in this invention. A hydrogenolysis reaction uses hydrogen to cleave the carbon-oxygen bond of either the 1,2 carbon-oxygen bond or the 2,3-carbon-oxygen bond by means of the supported noble metal catalyst. The purity of the hydrogen being fed to the reactor is high enough to effect the desired reaction and not contain significant amounts of impurities that could act as poisons or inhibitors. Inert hydrocarbons such as methane, ethane, propane and butane are managed by normal gas purging methods to keep the desired partial pressure of reactant hydrogen present in the reactor. For certain impurities such as carbon monoxide, methods such as nickel methanation catalyst beds and the like can be used to convert CO into an inert methane impurity and thereby control the concentration of CO in the reactor feed stream.

The amount of hydrogen fed in the continuous process can be that amount sufficient to enhance selectivity to the hydroxy ether mono-hydrocarbon. The amount of hydrogen used will vary depending on the reaction conditions and type of cyclic compound used as the substrate, but generally, a molar ratio of hydrogen to cyclic compound of at least 5:1 is suitable. Other examples of molar ratios of hydrogen to cyclic compounds include at least 10:1, or at least 50:1, or at least 100:1, or at least 150:1, or at least 170:1, or at least 190:1, or at least 200:1, or at least 250:1, and can be as high as desired. It is desirable to adjust the molar ratio to increase selectivity. The selectivity is improved with the catalyst compositions of the invention when the molar ratio exceeds 100:1, or is at least 125:1, or is at least 150:1.

The reactor pressures used may be from one atmosphere (14.7 psig) up to 5000 psig Higher reactor pressures have the advantage of reducing the formation of ester byproducts such as ethyl butyrate, ethylene glycol monobutyrate, and 2-n-butoxybutanol monobutyrate in the case where 2-propyl-1,3-dioxolane is used as the feed material. Particularly useful pressure ranges are within 200 to 1000 psig for practical operation of this invention.

The reactor design is not crucial for the operation of this invention. The reactor should be designed to permit a gaseous mixture of hydrogen and the cyclic compounds to pass over the supported noble metal catalyst and exit the reactor zone with the desired hydroxy ether hydrocarbon as a gaseous product mixture. Convenient designs include plug flow reactors such as long tubular designs and multi-tube short path designs. Other reactors known as "pancake" reactors have a wide continuous catalyst bed that is of a relatively short path. The process can also be conducted in exotic designs such as spinning basket or Berty type reactors can be used. In all reactor designs, however, the catalyst bed should remain at a temperature above the dew point of the reactants and products at the reactor conditions used. Additionally, the design of the reactor feed system should be designed to keep the feed composition compositionally balanced to that the partial pressures of the cyclic compounds fed to the reactor remain above the dew points of the cyclic compounds under the operating reactor conditions. This may be easily achieved by use of vapor liquid equilibrium feed chambers or by controlling the rates of liquid and hydrogen feed rate to the reactor via a mixing chamber to assure complete vaporization of the cyclic compounds at the reactor conditions prior to contact with the hydrogenolysis catalyst bed and to maintain the cyclic compounds at the proper feed partial pressure.

No polyhydroxyl hydrocarbon co-solvent feed, such as ethylene glycol, is required in a vapor phase hydrogenolysis conversion process. Thus, an advantage of the current process is conducting a conversion of cyclic compounds to their corresponding hydroxy ether hydrocarbon reaction products in the absence of a liquid solvent feed, such as ethylene glycol, at high selectivities.

The product stream is withdrawn from the reaction zone. The product stream contains a hydroxy ether reaction product of the cyclic compound(s) with hydrogen. The reaction zone reaction conditions can be set to ensure that the hydroxy ether reaction product remains above its dew point. The reaction conditions can also be set within the reaction zone to ensure that the product stream withdrawn from the reaction zone remains above its dew point and is a vapor. When the product stream is withdrawn from the reaction zone as a vapor, the product stream will also contain other types of compounds in minor amounts, such as by-products, hydrogen gas, and un-reacted cyclic acetal or ketal compounds.

In the vapor phase hydrogenolysis of the cyclic compounds over a heterogeneous supported noble metal catalyst, the noble metal catalyst is not withdrawn in the product stream. The product stream withdrawn advantageously does not contain any appreciable quantities of the noble metal catalyst that have to be separated from the desired hydroxy ether hydrocarbon. In one embodiment of the invention in the product stream withdrawn from the reaction zone contains less than 500 ppmw of the metal catalyst used in the reaction zone, or less than 100 ppmw, or less than 50 ppmw, or less than 25 ppmw, or less than 10 ppmw, or less than 5 ppmw, or less than 2 ppmw, based on the weight of all ingredients fed to the reaction zone.

Suitable hydroxy ether hydrocarbons are the reaction products of the cyclic compounds with hydrogen gas resulting in a hydrocarbon with at least one ether linkage and at least one primary hydroxyl group. The hydroxy ether hydrocarbons may contain secondary hydroxyl groups, and additional ether linkages. In one embodiment, the hydroxy ether hydrocarbons are represented by the general formula:

$$R^6OR^7OH$$

wherein $R^6$ is a branched or un-branched $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cylcoalkyl, or a $C_3$-$C_{50}$ carboxylate ester; and wherein the alkyl, alkenyl, aryl, and cycloalkyl groups of $R^6$ optionally contain 1, 2, or 3 oxygen atoms in the alkyl, cycloalkyl, or alkenyl group and are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol.

In the case that the cyclic compound starting material is a cyclic ketal, then $R^6$ branched at least at the carbon adjacent the ether linkage in the general formula above. The branch can be selected from the same groups as $R^6$.

$R^7$ is a branched or un-branched divalent $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cylcoalkyl, or a $C_3$-$C_{50}$ carboxylate ester; and wherein the divalent alkyl, alkenyl, aryl, and cycloalkyl groups of $R^7$ optionally contain 1, 2, or 3 oxygen atoms in the divalent alkyl, cycloalkyl, or alkenyl group and are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol.

The $R^6$ group of the general formula may be a branched or un-branched $C_1$-$C_{12}$ alkyl or aryl-$C_1$-$C_{12}$ alkyl; optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol.

The $R^7$ group of the general formula may be a divalent branched or un-branched $C_1$-$C_{12}$ alkyl or a $C_2$-$C_{12}$ alkenyl; and wherein the divalent alkyl or alkenyl groups of $R^7$ optionally contain 1, 2, or 3 oxygen atoms in the divalent alkyl or alkenyl groups and are optionally substituted with 1, 2, or 3 groups independently selected from —OH or halogen.

In each case above, the alkyl groups may have from 1-8 carbon atoms, or 1-6 carbon atoms, or 1-4 carbon atoms, and the alkenyl groups may have from 2-8 carbon atoms, or 2-6 carbon atoms, or 2-4 carbon atoms.

Examples of the types of hydroxy ether hydrocarbons that are made by the process of the invention include ethylene glycol propyl ether, ethylene glycol butyl ether, ethylene glycol 2-ethylhexyl ether, diethylene glycol methyl ether, diethylene glycol ethyl ether, diethylene glycol propyl ether, diethylene glycol butyl ether, propylene glycol methyl ether, ether, 3-butoxy-1,2-propanediol, 2-butoxy-1,3-propanediol, 2-isopropoxyethanol, isopropoxy-2-propanol, 3-isopropoxypropanol, 2-(3-methyl-2-butoxy)ethanol, 3-(3-methylbutan-2-yloxy)propanol, 2-(4-methylpentan-2-yloxy)ethanol, 3-(4-methylpentan-2-yloxy)propanol, 3-(4-methylpentan-2-yloxy)-1,2-propanediol, 2-(4-methylpentan-2-yloxy)-1,3-propanediol, 2-(pentan-2-yloxy)ethanol, 3-(pentan-2-yloxy)-propanol, 2-(pentan-2-yloxy)-1,3-propanediol, 3-(pentan-2-yloxy)-1,2-propanediol, 2-(methyl-hexyloxy)ethanol, 3-(methyl-hexyloxy)-propanol, 2-(methyl-hexyloxy)-1,3-propanediol, 3-(methyl-hexyloxy)-1,2-propanediol.

The hydroxy ether hydrocarbons have a wide variety of uses. They can be used as solvents, coalescents and plasticizers in all-purpose cleaners, architectural coatings, automotive coatings, cleaners for ink processes, coalescents for latex paints, coatings for plastics, floor cleaners, solvents for removing photoresists in semiconductor wafers, glass cleaners, household cleaners, industrial cleaners, industrial coatings, and metal brighteners and cleaners. They can be used a solvents for a large variety of coatings resin types, including alkyd, phenolic, maleic, epoxy, and nitrocellulose resins. They are also useful as retarder solvent for lacquers, improving gloss and flow-out. Some of the hydroxy ether hydrocarbons can also be used in amine-solubilized, water-dilutable coatings because of their high flash point, complete water solubility, slow evaporation rate, low surface tension, and high coupling efficiency. As coalescents, they improve film integrity in both architectural and industrial maintenance latex paints.

The desired hydroxy ether hydrocarbon can be readily separated from the product stream. One particularly useful method is to cool the gaseous reactor product stream to below the dew point of the reaction products and unreacted cyclic compounds to form a liquid product and from which a gaseous stream comprised primarily of hydrogen gas (greater than 70 vol. %) is easily separated. When the cooling is carried out at reactor pressure, very little energy is required to re-circulate the un-reacted hydrogen back as a feedstock reactant stream to the reactor vessel. The condensed liquid products may then be recovered and purified by known methods, such as distillation, extraction, crystallization and the like to obtain the desired product. Similarly, a liquid scrubber may be employed to recover condensable liquid products from the gaseous reactor effluent. These and other known methods of product recovery may be used in combination with the hydrogenolysis process of this invention.

The process of the invention is carried out batchwise or continuously, preferably continuously.

WORKING EXAMPLES

The liquid feed part of the unit consists of a 100 mm graduated burette feed tank for the acetal feed. This is connected to a flow programmable high pressure lab scale ball and check feed pump (Eldex ReciPro Optos Series Model 1). All equipment under pressure is constructed of 316 stainless steel tubing or fittings. The discharge of the pump leads to ⅛ inch diameter tubing that is connected to a fitting on the top of a preheater section. The preheater is constructed of ¼ inch outer diameter tubing. The tubing is packed with fused alumina. A thermocouple extends into the alumina bed to allow for monitoring of the internal temperature. The preheater is wrapped with electrical heating tape controlled by an adjustable thermostat. The internal temperature of the preheater is maintained +/−5° C. of the desired reaction temperature. The exit of the preheater is connected to a fitting on the top of the reactor. This fitting is further connected to a ⅛ inch diameter tubing section that leads to a vaporization section prior to the catalyst bed. Hydrogen feed is supplied from high pressure cylinders of zero grade hydrogen via a high pressure regulator to a lab scale Brooks mass flow controller. Nitrogen feed, used for purging and other inert gas needs, is fed by a similar design from a high pressure cylinder via a gas regulator through another dedicated Brooks mass flow controller for inert gas flow. The discharges from these two mass flow controllers are connected by a manifold to a ¼ inch diameter tubing feed line that is connected to the top of the reactor. The hydrogen or inert gas feeds enter the reactor by an annulus around the ⅛ inch diameter liquid feed line and mix with the liquid above the vaporization section in the reactor.

The reactor is a 24" long×½" diameter section of high pressure tubing held in a vertical arrangement. The top part of the reactor consists of a stainless steel Swagelok cross with the appropriate fittings required to permit liquid feed to the reactor via the ⅛ inch diameter tubing, to permit hydrogen or other gas feed to the reactor via ¼ inch tubing and to connect to a pressure gage and a safety pressure relief device. The top portion of the reactor consists of a bed 4" deep of fused alumina beads 2-3 mm in diameter that are used for the vaporization of the liquid feed in contact with the gaseous hydrogen feed. A thermocouple is attached to the outside skin of the reactor about 1" from the bottom of the vaporization bed and is externally wrapped with heat resistant insulation tape to measure the skin temperature of the metal surface as being heated from the inside by the heated gases. A spacer of pyrex wool packing is used to separate the vaporizer section from the catalyst section of the bed that is downstream from the vaporizer. The lab unit normally uses 10 cubic centimeters of the hydrogenation catalyst used in this invention. The depth of the bed is approximately 5 inches deep. The bed is held in place by another spacer of pyrex wool packing and a support of ¼ inch diameter tubing to hold it in place. A second thermocouple is attached with similar insulation to the outer skin of the reactor tubing about 2 thirds of the depth of the catalyst bed towards the bottom. A third K-type thermocouple extends from the exit of the reactor into the reactor to a depth of approximately ½ inch of the bottom of the catalyst bed. The reactor tubing is placed inside a "clam shell" heater that is electrically heated and controlled by the temperature recorded by the thermocouple extending into the catalyst bed.

The ½ tubing of the bottom of the reactor is connected by appropriate Swagelok fittings to a 1" 316 stainless steel "T". This "T" is filled with ⅛" stainless steel Penn State packing material as a coalescer and is cooled by way of a circulating bath to copper tubing on the outside of the "T". This "T" is a high pressure vapor/liquid (V/L) separator where liquid product is condensed for recovery. The bottom of the "T" has a needle valve connected to a small section of ⅛" diameter tubing where the collected liquid product is drained periodically and analyzed by gas chromotograph. The side fitting of the "T" consists of ½ tubing that provides an exit for the uncondensed hydrogen and other gases. The side fitting also has a thermocouple in it to measure the inside temperature of the "T". The gases leaving the side tubing of the "T" are then directed upwards to a back pressure regulator that controls the pressure of the reactor. Gases leaving downstream from the back pressure regulator are at ambient pressure and proceed to an on-line gas chromatograph that allows for analysis of non-condensed products.

Example 1

Hydrogenolysis Of 2-propyl-1,3-dioxolane Over 1% Pd/1000 ppmNi on Alumina

The liquid feed tank of the unit was filled with a cyclic acetal of this invention, 2-n-propyl-1,3-dioxolane (PDX). The reactor had been charged with 10 cc (8.5 grams) of a catalyst containing 1% Pd/1000 ppmw Ni on alumina sphere supplied by BASF (SEO86630). The hydrogen flow was set at 7950 sccm and the back pressure regulator was set to 500 psig. The catalyst bed temperature target was set at 210 degrees Celsius. After reaching 210 degrees, the reactor was permitted to equilibrate at 210 degrees Celsius for fifteen minutes. After that period, the PDX pump was started with a target feed rate of 0.28 ml/minute. Liquid product samples were collected hourly as was operating data. The samples were weighed and analyzed by gas chromatographic analysis on Agilent Technologies 7890A series machine having a thermal conductivity detector. The column used was a 30 m J & W 122-3232 DB-FFAP capillary column. A 2 minute hold was used at 50 degrees C. followed by a 10 deg/min heat up rate to a final temperature of 250 deg C. and a final 10 minute hold at 250 deg. C. Response factors were used in normal standard practice to obtain the weights of the different components.

The last five hours of samples and feed level drop were used to perform calculations on the conversion of PDX into the desired product 2-n-butoxyethanol. A total of 79.9 g of PDX was fed during this period. A total of 24.3 grams of PDX was recovered, 51.4 grams of 2-n-butoxyethanol, 0.18 grams of ethyl butyrate, 0.07 g of normal butanol, 2.38 g of 1,2-n-butoxyethane, 0.29 grams of methyl-n-butylether, 0.35 g of 2-n-butoxyethanol monobutyrate ester, 0.85 grams of ethylene glycol and 0.08 grams of other organic materials were recovered. The conversion of the PDX was 79% with a selectivity of consumed PDX to 2-n-butoxyethanol of 92.6%. The H2/PDX feed mole ratio of this run was 160:1 with the PDX partial pressure in the reactor at 165 mm Hg and a catalyst residence time of 1.5 seconds. The specific production rate of the desired 2-n-butoxyethanol was 64 lb/ft$^3$·h.

Example 2

Varying Process Conditions

The Table 1 of runs below used the same charge of catalyst, namely a 10 cc sample of BASF Catalysts 1% Pd/0.1% Ni alumina sphere catalyst (SEO86630) in the above described unit and demonstrates the effect of various reaction parameters on per pass conversion and selectivity.

TABLE 1

| Run | Temp (° C.) | H2/PDX | Psig | PDX, cc/min | gas, sccm | Conversion | EB Selectivity | glyme Selectivity | Ester Selectivity | MBE Selectivity | BuOH Selectivity |
|---|---|---|---|---|---|---|---|---|---|---|---|
| 2 | 195 | 170 | 300 | 0.10 | 3200 | 85.3% | 90.5% | 7.0% | 1.5% | 0.38% | 0.59% |
| 3 | 230 | 80 | 500 | 0.58 | 8535 | 73.3% | 93.4% | 4.5% | 0.64% | 1.2% | 0.12% |
| 4 | 230 | 150 | 500 | 0.40 | 10600 | 77.3% | 88.5% | 7.5% | 1.8% | 1.7% | 0.32% |

PDX = 2-n-propyl-1,3-dioxolane; EB = 2-n-butoxyethanol; MBE = methyl-n-butylether; ester = ethyl n-butyrate and EB monobutyrate; glyme = 1,2-di-n-butoxyethane.

Comparative Example 1

Use of an Un-Promoted 1% Pd/Alumina Catalyst

Unpromoted catalysts having a Pd loading of 1% or greater tend to be very active, but not as selective as the nickel promoted catalysts as indicated in these comparative examples.

The reaction was carried out as described above with a 10 cc charge of 1% Pd on ⅛" alumina spheres (BASF Catalysts 1% Pd AS-38). The last five hours of samples and feed level drop were used to perform calculations on the conversion of PDX into the desired product 2-n-butoxyethanol. A total of 77.2 g of PDX was fed during this period. A total of 3.4 grams of PDX was recovered, 59.3 grams of 2-n-butoxyethanol, 0.02 grams of ethyl butyrate, 0.19 g of normal butanol, 9.5 g of 1,2-n-butoxyethane, 0.21 grams of methyl-n-butyl ether, 0.30 g of 2-n-butoxyethanol monobutyrate ester, 3.36 grams of ethylene glycol and 0.20 grams of other organic materials were recovered. The conversion of the PDX was 99% with a selectivity of consumed PDX to 2-n-butoxyethanol of 80.9% and a selectivity of consumed PDX to 1,2-dibutoxyethane of 17.6%. The specific production rate of the desired 2-n-butoxyethanol was 74 lb/ft$^3$·h.

Comparative Example 2

Varying Process Conditions

The table below shows the reduced selectivity of the catalyst of Comparative Example 1 at other reaction conditions along with the high production of undesired byproducts such as 1,2-dibutoxyethane and its co-produced ethylene glycol.

TABLE 2

| Run | Temp (° C.) | H2/ PDX | psig | PDX, cc/min | gas, sccm | Conversion | EB Selectivity | glyme Selectivity | Ester Selectivity | MBE Selectivity | BuOH Selectivity |
|---|---|---|---|---|---|---|---|---|---|---|---|
| 6 | 195 | 170 | 300 | 0.10 | 3200 | 100% | 82.4% | 15.6% | 0.97% | 0.44% | 0.32% |
| 7 | 195 | 170 | 300 | 0.20 | 6400 | 91.5% | 63.8% | 34.5% | 1.3% | 0.20% | 0.04% |
| 8 | 210 | 150 | 500 | 0.42 | 11670 | 94.3% | 75.2% | 24.4% | 0.19% | 0.15% | 0.06% |

Comparative Example 3

Use of Un-Promoted Catalysts with Less than 1% Pd

The reaction was carried out as described above with a 10 cc charge of 0.5% Pd on 1/16" alumina spheres from Evonik Degussa (Evonik E2123) The last five hours of samples and feed level drop were used to perform calculations on the conversion of PDX into the desired product 2-n-butoxyethanol. A total of 77.9 g of PDX was fed during this period. A total of 42.4 grams of PDX was recovered. 31.5 grams of 2-n-butoxyethanol, 0.02 grams of ethyl butyrate, 1.25 g of 1,2-n-butoxyethane, 0.01 grams of methyl-n-butyl ether, 0.20 g of 2-n-butoxyethanol monobutyrate ester, 0.47 grams of ethylene glycol and 0.13 grams of other organic materials were recovered. The conversion of the PDX was 58.3% with a selectivity of consumed PDX to 2-n-butoxyethanol of 94.5% and a selectivity of consumed PDX to 1,2-dibutoxyethane of 5.07%. The specific production rate of the desired 2-n-butoxyethanol was 39 lb/ft$^3$·h. These catalysts have very high selectivity to the desired glycol ether, but a lower rate of production than the 1% catalysts.

Comparative Example 4

Use of 1% Pd Catalyst Promoted with Ni and Na

The reaction was carried out as described above with a 10 cc charge of 1% Pd/0.1% Ni/###% Na on 1/8" alumina spheres (BASF Catalysts SEO #9582). A total of 79.3 g of PDX was fed during this period. A total of 55.3 g of PDX was recovered. 20.8 g of 2-ethoxybutanol, 0.25 grams of ethyl butyrate, 0.89 g of 1,2-n-butoxyethane, 0.40 grams of methyl-n-butyl ether, 0.19 g of 2-n-butoxyethanol monobutyrate ester, 0.23 grams of ethylene glycol and 0.09 grams of other organic materials were recovered. The conversion of the PDX was 39.9% with a selectivity of consumed PDX to 2-n-butoxyethanol of 90.4%. The specific production rate of the desired 2-n-butoxyethanol was 26 lb/ft$^3$·h. The per pass conversion of this catalyst is too low to be industrially relevant.

What we claim is:

1. A process comprising:
   (a) contacting cyclic compounds with hydrogen in the presence of a catalyst composition in a reaction zone to produce a vapor hydroxy ether hydrocarbon,
   (b) withdrawing from the reaction zone a vapor product stream comprising a vapor hydroxy ether hydrocarbon and hydrogen, and
   (c) separating and recovering a hydroxy ether hydrocarbon composition from the product stream,
   wherein said cyclic compounds comprise a cyclic acetal, a cyclic ketal, or a combination thereof, and
   wherein the catalyst composition comprises an aluminum oxide support containing or on which is deposited 0.8 to 5 wt % of palladium and 500 to 3,000 ppmw of nickel, based on the weight of the catalyst composition.

2. The process of claim 1, wherein the conversion of cyclic compounds is at least 70% and the selectivity to the production of hydroxy ether monohydrocarbons is at least 85%.

3. The process of claim 2, wherein the selectivity is at least 90%.

4. The process of claim 3, wherein the conversion is at least 75%.

5. The process of claim 4, wherein the cyclic compound comprises a cyclic acetal.

6. The process of claim 1, wherein a diether co-product is generated in an amount of less than 5 wt %.

7. The process of claim 1, wherein the reaction zone conditions are above the dew point of product stream.

8. The process of claim 1, wherein the reaction in the reaction zone is conducted in the absence of a liquid compound.

9. The process of claim 1, wherein the cyclic compound comprises 2 propyl-1,3-dioxolane.

10. The process of claim 1, wherein the temperature of the reaction zone is at least 180° C.

11. The process of claim 10, wherein the partial pressure within the reaction zone is above the dew point of all the cyclic compounds within the composition fed to the reaction zone at reaction zone temperature.

12. The process of claim 1, wherein the selectivity to the hydroxy ether compounds is at least 90 mole %.

13. The process of claim 1, wherein the cyclic compounds have a practical vapor pressure in excess of 10 mm Hg at the temperature within the reaction zone.

14. The process of claim 13, wherein the practical vapor pressure of the cyclic compounds is at least 50 mm Hg at the temperature within the reaction zone.

15. The process of claim 13, wherein the temperature within the reaction zone is within a range of 180° C. to 250° C.

* * * * *